United States Patent [19]
Ferguson et al.

[11] Patent Number: 5,960,808
[45] Date of Patent: Oct. 5, 1999

[54] METHOD OF CONTROLLING THE AMOUNT OF SANITIZING AGENT IN AN AQUEOUS MEDIUM

[75] Inventors: Richard H. Ferguson, New Martinsville; Gerald E. Moore, Sistersville, both of W. Va.; Stanley R. Pickens, Monroeville, Pa.

[73] Assignee: PPG Industries Ohio, Inc., Cleveland, Ohio

[21] Appl. No.: 08/877,842

[22] Filed: Jun. 18, 1997

[51] Int. Cl.$^6$ .................................................. G05D 11/08
[52] U.S. Cl. .............................. 137/5; 137/93; 137/599.1; 137/89
[58] Field of Search .................... 137/5, 89, 93, 137/599.1, 599

[56] References Cited

U.S. PATENT DOCUMENTS

| | | | |
|---|---|---|---|
| 1,388,613 | 8/1921 | Simsohn | 137/5 |
| 3,107,156 | 10/1963 | Fredricks | 23/267 |
| 3,203,440 | 8/1965 | Schneider, Jr. | 137/268 |
| 3,426,901 | 2/1969 | Sherper | 210/169 |
| 3,474,817 | 10/1969 | Bates et al. | 137/268 |
| 3,595,395 | 7/1971 | Lorenzen | 210/169 |
| 3,820,014 | 6/1974 | Ludt | 137/5 |
| 3,846,078 | 11/1974 | Brett | 23/267 |
| 3,864,090 | 2/1975 | Richards | 23/267 |
| 3,899,425 | 8/1975 | Lewis | 210/206 |
| 3,956,094 | 5/1976 | Capuano | 204/195 |
| 4,323,092 | 4/1982 | Zabel | 137/5 |
| 4,331,174 | 5/1982 | King, Sr. | 137/268 |
| 4,366,064 | 12/1982 | Mihelic et al. | 210/668 |
| 4,407,322 | 10/1983 | Moore et al. | 137/268 |
| 4,435,291 | 3/1984 | Matsko | 210/739 |
| 4,548,228 | 10/1985 | Moore et al. | 137/268 |
| 4,584,106 | 4/1986 | Held | 210/754 |
| 4,732,689 | 3/1988 | Harvey et al. | 210/754 |
| 4,759,314 | 7/1988 | Banweg | 137/89 |
| 4,759,907 | 7/1988 | Kawolics et al. | 422/7 |
| 4,867,196 | 9/1989 | Zetena et al. | 137/268 |
| 4,927,546 | 5/1990 | Wiedrich et al. | 210/755 |
| 5,089,127 | 2/1992 | Junker et al. | 210/206 |
| 5,284,174 | 2/1994 | Norman | 137/5 |
| 5,295,505 | 3/1994 | Polaschegg | 137/93 |
| 5,384,102 | 1/1995 | Ferguson et al. | 422/264 |
| 5,447,641 | 9/1995 | Wittig | 210/756 |
| 5,460,446 | 10/1995 | Chevallet | 137/5 |
| 5,611,937 | 3/1997 | Jarocki | 210/754 |
| 5,823,219 | 10/1998 | Purvis et al. | 137/5 |

OTHER PUBLICATIONS

*Standard Methods for the Examination of Water and Wastewater*, 19th edition, 1995, American Public Health Association, pp. 4–46 to 4–45.

Primary Examiner—John Rivell
Assistant Examiner—Raymar Farid
Attorney, Agent, or Firm—James R. Franks; Irwin M. Stein

[57] ABSTRACT

A method of controlling the amount of conductivity increasing substances, e.g., free available halogen, in particular free available chlorine, present in an aqueous medium is described. In accordance with the method of the present invention, an aqueous medium is provided and its conductivity determined. A source of at least one conductivity increasing substance is introduced controllably into the aqueous medium, and a second conductivity measurement is made. The determined conductivities are compared, and in response to this comparison, the amount of conductivity increasing substance added to the aqueous medium is adjusted. In a preferred embodiment of the present invention, the aqueous medium is an aqueous stream, and the source of conductivity increasing substance is calcium hypochlorite, which is introduced into the aqueous stream through the use of a feeder unit, i.e., a chlorination unit.

17 Claims, 3 Drawing Sheets

METHOD OF CONTROLLING THE AMOUNT OF SANITIZING AGENT IN AN AQUEOUS MEDIUM

DESCRIPTION OF THE INVENTION

The present invention is directed generally to a method of controlling the amount of conductivity increasing substances present in an aqueous medium by controlling the amount of such substances added to the aqueous medium. In particular the method of the present invention makes use of the electrical conductivity of an aqueous medium to control the amount of conductivity increasing substance present therein. More particularly, the present invention is used to control the amount of free available halogen present in an aqueous stream. The present invention is also directed to a method of sanitizing a surface of an article, which method comprises contacting such surface with an aqueous medium containing a sanitizer, the concentration of which is regulated by the aforedescribed method.

The controlled addition of conductivity increasing substances, for example, acids, bases, salts, and other halogen-containing materials, to an aqueous stream in order to establish a desired level of such substances therein is useful in a number of applications, such as, sanitizing an aqueous stream, increasing the acidity of an aqueous stream, increasing the basicity of an aqueous stream or increasing the salinity of an aqueous stream. The sanitization of an aqueous stream typically involves the addition of a halogen or halogen-containing material, e.g., chlorine or calcium hypochlorite, to the stream to establish a desired level of free available halogen, e.g., free available chlorine, in the aqueous stream. The presence of free available halogen within the aqueous stream serves to eradicate deleterious amounts of bacteria that may be present. Ingestion of or even topical exposure to unsanitized or inadequately sanitized water having bacteria therein can lead to sickness and disease in animals and humans. Further, the ingestion by animals and humans of unsanitized or inadequately sanitized foods, or foods that have been processed on unsanitized or inadequately sanitized surfaces, e.g., harvested fruits and poultry products, can lead to sickness and disease in animals and humans.

Drinking water typically contains from 0.5 to 1 part free available chlorine (FAC) per million parts of water (ppm). Free available chlorine can be introduced into water by adding a source of hypochlorous acid (HOCl) or hypochlorite anion (ClO$^-$) into the water. Recreational bodies of water, e.g., swimming pools, hot tubs, spas, etc., typically contain from 1 to 3 ppm of FAC. Water having a FAC content in amounts of greater than 10 ppm can be used to sanitize surfaces or articles to which it is applied.

Controlling the amount of free available halogen, in particular free available chlorine, in an aqueous stream or body of water is important. For example, if too much FAC is present in drinking water, it will become undrinkable. If too little FAC is present in an aqueous stream which is to be used for sanitizing a surface, e.g., by spray application, the surface may not be adequately sanitized.

A common method of controlling the amount of free available chlorine present in an aqueous stream involves oxidation-reduction potential analysis of the aqueous stream. Typically, this involves passing the aqueous stream in which FAC is present past a pair of electrodes. The electrodes develop an electrical potential upon exposure to oxidizing and reducing species in the aqueous stream, e.g., FAC. This electrical potential is typically related to the amount of FAC present in the aqueous stream—the relationship being indicated mathematically by the Nernst equation. The amount of FAC detected dictates whether more or less FAC or FAC producing substance is added to the aqueous stream. Oxidation-reduction potential analysis becomes less sensitive and unreliable when the FAC content of an aqueous stream or body of water exceeds 2 ppm, and in particular when it exceeds 10 ppm.

Another method of controlling the amount of free available chlorine present in an aqueous stream involves regulating the flow rate of an aqueous stream through a chlorination unit. The flow rate is set based on a previously determined correlation between different flow rates through the chlorination unit and the resulting amounts of FAC present in the aqueous stream. The correlation information is typically supplied by the manufacturer of the chlorination unit. The draw back of such a method is that it can be unreliable. In particular if the operating efficiency of the chlorination unit drifts or degrades with time, either too much or too little of the FAC source will be added to the aqueous stream.

U.S. Pat. No. 4,323,092 discloses an apparatus and process for measuring and monitoring the free active chlorine content of an aqueous solution, e.g., drinking or bathing water. The apparatus preferably utilizes a measuring cell, which measures the amount of free active chlorine by an amperometric or coulometric process. The measuring cell is connected to an electrical comparison circuit, which controls a regulator or magnetic valve, in order to control the amount of active chlorine in the system.

U.S. Pat. No. 5,447,641 discloses a poultry water chlorinator and a method of using same. An in line chlorinator having solid calcium hypochlorite placed therein is provided. The chlorinator is used to dissolve the solid calcium hypochlorite in water, dilute it to a desired concentration, and dispense it at a flow rate in the range of approximately 50 to 3500 gallons/day.

U.S. Pat. No. 5,611,937 discloses a method and apparatus for treating water in which water from a local supply is mixed with measured quantities of a chlorine disinfectant and introduced into a holding vessel, carbon dioxide is also added to the holding vessel. A treating module, having a flow sensor therein, is governed by a microprocessor which affects the mixing of disinfectant and water.

It would be desirable to have a relatively simple, cost effective and accurate method of controlling the amount of conductivity increasing substances added to an aqueous stream, e.g., a source of free available halogen, and in particular free available chlorine in amounts in excess of 10 ppm.

In accordance with the present invention there is provided a method of controlling the amount of conductivity increasing substance present in an aqueous medium, comprising the steps of:

(a) providing an aqueous medium;

(b) determining the electrical conductivity of said aqueous medium;

(c) introducing controllably a source of at least one conductivity increasing substance into said aqueous medium;

(d) determining the electrical conductivity of the aqueous medium of step (c);

(e) comparing the electrical conductivities determined in steps (b) and (d); and (f) adjusting in response to the comparison of step (e) the introduction of said conductivity increasing substance into said aqueous medium.

In accordance with another embodiment of the present invention there is provided a method of controlling the amount of conductivity increasing substance present in an aqueous stream, comprising the steps of:

(a) providing a feeder unit having therein a source of at least one conductivity increasing substance;

(b) providing an aqueous stream;

(c) splitting said aqueous stream into a first aqueous stream and a second aqueous stream;

(d) introducing controllably said first aqueous stream into said feeder unit and into contact with said conductivity increasing substance;

(e) removing a third aqueous stream from said feeder unit, said third aqueous stream containing said conductivity increasing substance;

(f) combining said third aqueous stream with said second aqueous stream to form a fourth aqueous stream;

(g) determining the electrical conductivities of the aqueous stream of step (b) and of said fourth aqueous stream;

(h) comparing the conductivities determined in step (g); and (i) adjusting in response to the comparison of step (h) the introduction of said first aqueous stream into said feeder unit, thereby controlling the amount of said conductivity increasing substance present in said fourth aqueous stream.

In a further embodiment of the present invention there is provided a method of sanitizing a surface comprising:

(a) controlling the amount of free available halogen present in an aqueous stream by the steps of:
  (i) providing a halogenation unit having therein a source of free available halogen;
  (ii) providing an aqueous stream;
  (iii) splitting said aqueous stream into a first aqueous stream and a second aqueous stream;
  (iv) introducing controllably said first aqueous stream into said halogenation unit and into contact with said source of free available halogen;
  (v) removing a third aqueous stream from said halogenation unit, said third aqueous stream containing free available halogen;
  (vi) combining said third aqueous stream with said second aqueous stream to form a fourth aqueous stream;
  (vii) determining the electrical conductivities of the aqueous stream of step (a)(ii) and of said fourth aqueous stream;
  (viii) comparing the conductivities determined in step (a)(vii); and
  (ix) adjusting in response to the comparison of step (a)(viii) the introduction of said first aqueous stream into said halogenation unit, thereby controlling the amount of free available halogen present in said fourth aqueous stream; and (b) applying said fourth aqueous stream to a surface to be sanitized.

The features that characterize the present invention are pointed out with particularity in the claims which are annexed to and form a part of this disclosure. These and other features of the invention, its operating advantages and the specific objects obtained by its use will be more fully understood from the following detailed description and the accompanying drawings in which preferred embodiments of the invention are illustrated and described, and in which like reference characters designate corresponding parts.

Other than in the operating examples, or where otherwise indicated, all numbers expressing quantities of ingredients or reaction conditions used in the specification and claims are to be understood as modified in all instances by the term "about".

DETAILED DESCRIPTION OF THE INVENTION

Figure 1:
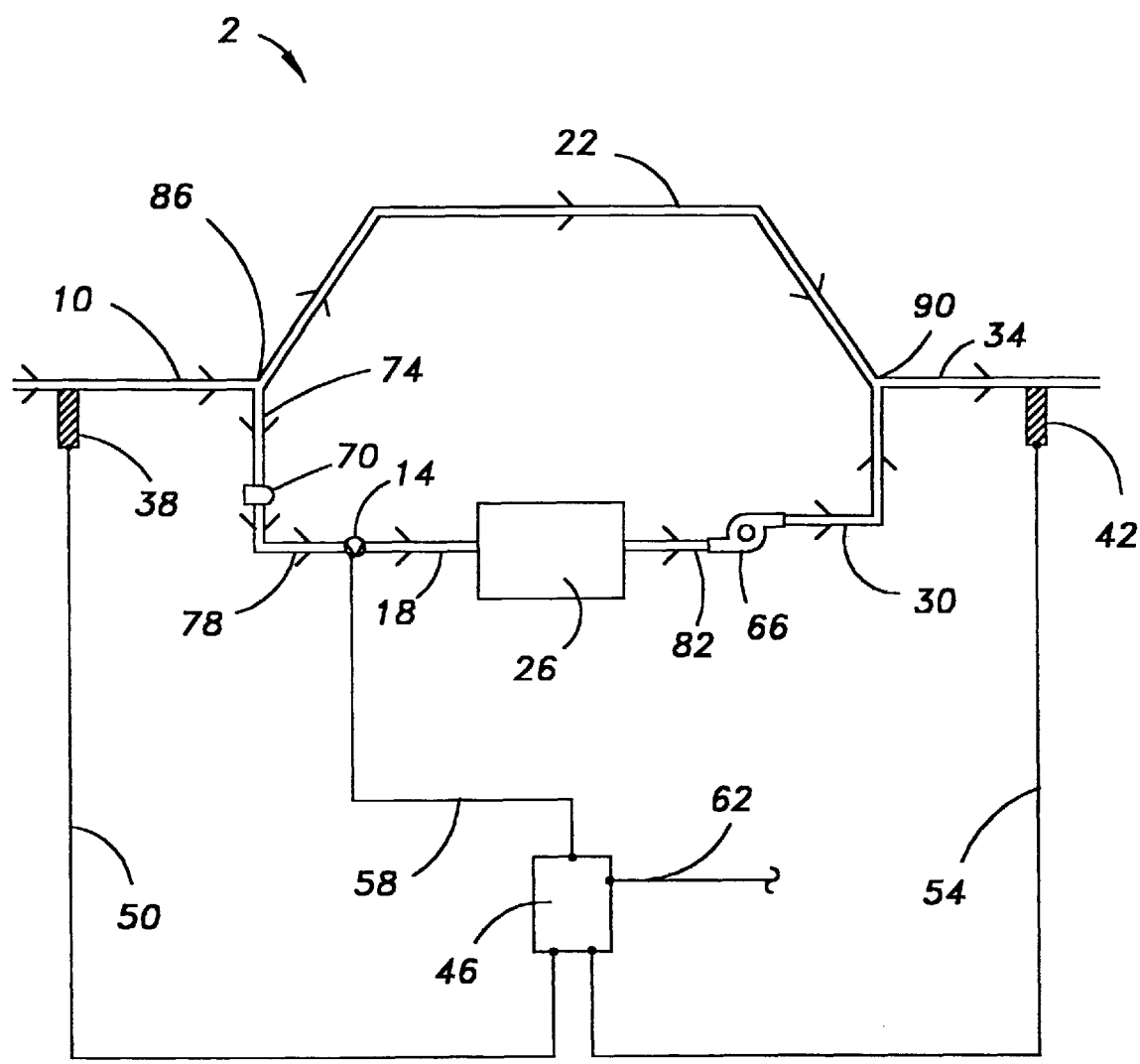
FIG. 1 is a schematic representation of an embodiment of the method of the present invention.

In describing embodiments of the present invention represented by illustration in the drawings, specific terminology is employed for the sake of clarity. However, the invention is not intended to be limited to the specific terminology so selected, and it is understood that each specific element includes all technical equivalents which operate in a similar manner to accomplish a similar purpose.

Referring now to FIG. 1 of the drawings, an aqueous stream distribution system 2 is represented. A feeder unit 26 is provided with a source of at least one substance which when added to a aqueous stream increases the conductivity of said stream. In a particularly preferred embodiment of the present invention, the feeder unit 26 is a low pressure chlorination unit having a source of free available chlorine therein, e.g., calcium hypochlorite. An aqueous stream from a source not shown is forwarded by means of conduit 10 to a juncture 86. The aqueous stream passing through conduit 10 is split into a first aqueous stream, which passes through conduit 74, and a second aqueous stream, which passes through conduit 22.

The first aqueous stream passes through pressure regulator 70, which acts to reduce the pressure of, and minimize pressure fluctuations in, the first aqueous stream to levels that are optimum for the operation of the feeder unit 26. If the feeder unit 26 is a high pressure unit, or a pressurized unit, then the pressure regulator 70 can be adjusted accordingly, or bypassed by a conduit not shown, or replaced by a pressure booster not shown.

The first aqueous stream exits the pressure regulator 70 and passes through conduit 78 to valve 14. Introduction of the first aqueous stream into feeder unit 26 by way of conduit 18 is controlled by valve 14. Valve 14 may be operated either manually or preferably by remote control in which case valve 14 is a remotely controlled valve, e.g., an electrically controlled valve. When valve 14 is an electromagnetically controlled valve it can be connected to an external power source by an electrical connection not shown. Within feeder unit 26, the first aqueous stream comes into contact with the source of the conductivity increasing substance, e.g., calcium hypochlorite. As a result, a conductivity increasing substance, e.g., free available chlorine, is added to the first aqueous stream, which is removed from the feeder unit as a third aqueous stream. The third aqueous stream having a conductivity increasing substance added thereto, e.g., free available chlorine, is removed from the feeder unit 26 through conduit 82. The third aqueous stream is forwarded by way of conduit 82 through a pressure boosting pump 66. The pressure boosting pump 66 is used to increase the pressure of the third aqueous stream to a level that is at least equivalent to that of the aqueous stream forwarded through conduit 10. If the feeder unit is a high pressure unit, the pressure boosting pump 66 may be bypassed by a conduit not shown, or replaced by a pressure regulator not shown.

The operation of pressure boosting pump 66 can be coordinated with that of valve 14 by an electrical connection from valve 14 to pump 66, or an electrical connection from process controller 46 to pump 66, neither being shown. For example, if valve 14 is closed, then pump 66 would be turned off. In an alternative embodiment of the present invention, the third aqueous stream is forwarded from conduit 82 into a collection tank not shown, from which tank pump 66 draws the collected third aqueous stream through a conduit not shown. The operation of pump 66 may be controlled by the level of the third aqueous stream collected within the collection tank, e.g., by means of a float control device not shown.

The third aqueous stream exits the pressure boosting pump 66 through conduit 30 and is combined with the second aqueous stream passing through conduit 22 at juncture 90 to form a fourth aqueous stream that has the conductivity increasing substance from feeder unit 26 present therein, e.g., free available chlorine. The fourth aqueous stream is forwarded through conduit 34 to the point of application (not shown). To ensure that the second aqueous stream does not flow from conduit 22 into conduit 30, a back-flow restriction device, e.g., a ball check valve, not shown, may be incorporated into conduit 30.

Figure 3:
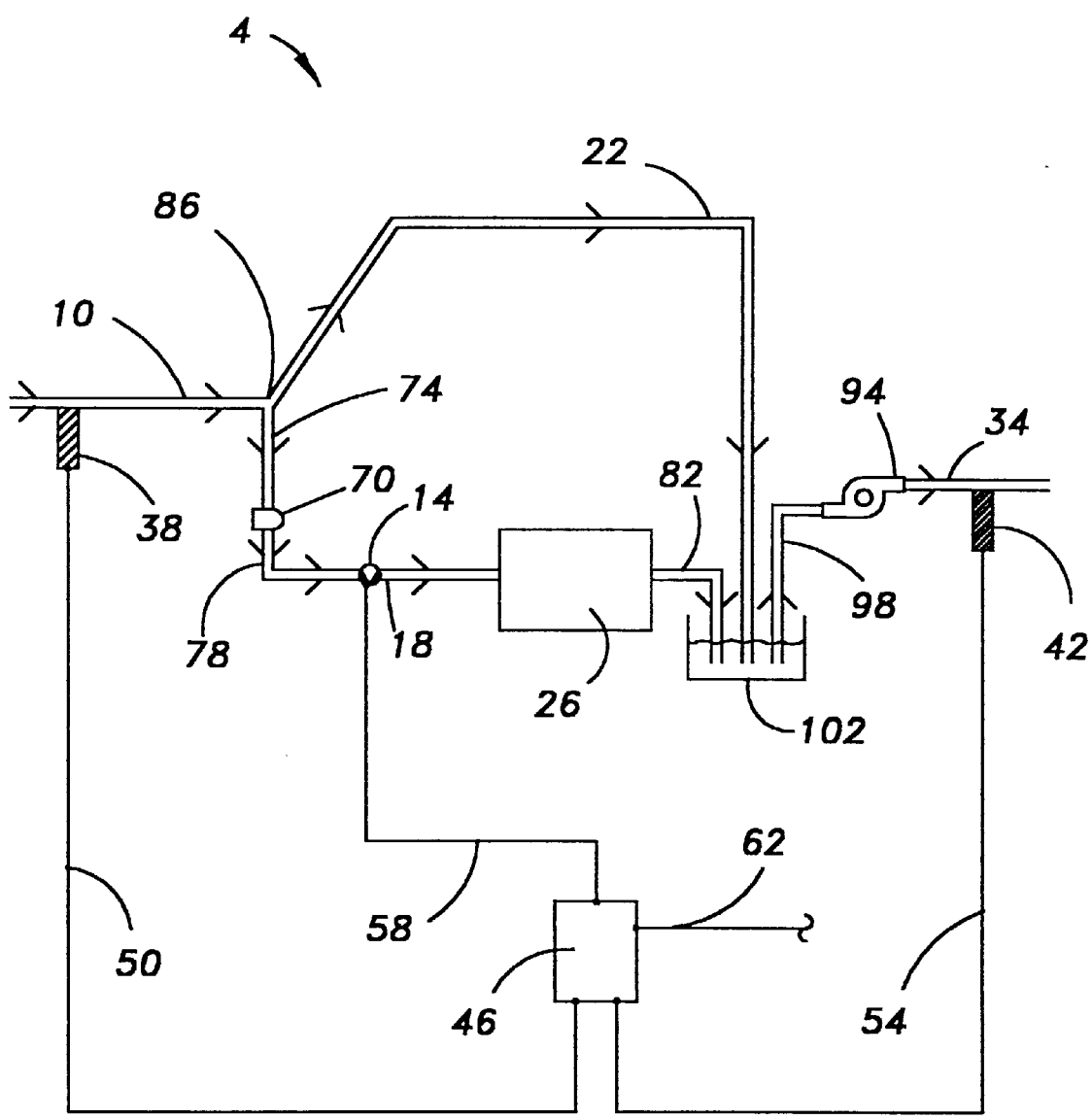
FIG. 3 is a schematic representation of another embodiment of the method of the present invention.

In another embodiment of the present invention, as represented by FIG. 3 of the drawings, an aqueous stream distribution system 4 is provided. The third and second aqueous streams are each forward through conduits 82 and 22 respectively into collection tank 102. The contents of collection tank 102 are removed through conduit 98 by pump 94, which may be a pressure boosting pump, and the fourth aqueous stream is forwarded from pump 94 through conduit 34.

Conductivity probes 38 and 42 are used to determine the electrical conductivities of the aqueous stream passing through conduit 10 and the fourth aqueous stream passing through conduit 34 respectively. The conductivity probes 38 and 42 may each be inserted directly into conduits 10 and 34 respectively. Alternatively the probes may each comprise a separate sampling cell through which a portion of the respective aqueous streams is continuously passed by way of bypass conduits not shown. The conductivity probe 38 may also be inserted into any of conduits 22, 74, 78 or 18. Furthermore a plurality of conductivity probes, not shown, may be inserted into any combination of conduits 22, 74, 78 and 18. The output signals from such a plurality of probes can be used either individually or in combination to form an averaged conductivity value of the aqueous stream prior to its having the conductivity increasing substance added thereto.

The electrical conductivities determined from conductivity probes 38 and 42 are compared to determine the amount of conductivity increasing substance added to the fourth aqueous stream. The comparison involves subtracting the conductivity value determined by probe 38 from that determined by probe 42. The comparison further involves using the difference in electrical conductivities with an equation derived from a previously generated calibration curve to calculate the amount of conductivity increasing substances added to the fourth aqueous stream.

When feeder unit 26 is a chlorination unit having calcium hypochlorite therein, the calibration curve is comprised of a substantially linear plot of the concentration of free available chlorine (FAC) vs. the difference in electrical conductivity measurements. The calibration curve is generated, for example, by adding known amounts of FAC to a given volume of aqueous solution, and recording the increase in electrical conductivity relative to the initial conductivity of the aqueous solution prior to the addition of FAC. A linear equation is obtained from the calibration curve, as represented by the following equation:

$$Y=mX+B \qquad \text{equation I}$$

wherein Y represents the amount of FAC added to the aqueous solution, m represents the slope of the linear calibration curve, X represents the difference in electrical conductivities, and B represents the value of the intercept of the linear line with the Y axis.

For ease of interpretation, it is preferable that the correlation between the conductivity difference and the amount of conductivity increasing substance added to an aqueous medium be a linear one. However, it is understood that the method of the present invention is also applicative to non-linear correlations. Whether the correlation is linear or nonlinear, it is important that it be continuous and reproducible over the range of amounts of conductivity increasing substance desired to be added to the aqueous medium.

The conductivity difference determined from probes 38 and 42 can be input into Equation I and the corresponding amount of FAC added to the aqueous stream calculated. In response to the calculated amount of FAC added, valve 14 can be adjusted accordingly to either increase or decrease the flow rate of the first aqueous stream into the feeder unit, e.g., chlorination unit, 26, thus increasing or decreasing the amount of conductivity increasing substances, e.g., FAC, added to the aqueous stream. It is also contemplated that the manner in which the aqueous stream contacts the conductivity increasing substance can be altered to vary the amount of such substance which is added to the aqueous stream. The rate of flow and manner of contact can be changed individually or both can be changed together.

Comparison of the electrical conductivities determined by probes 38 and 42 and adjustment of the valve 14 may be done manually or preferably automatically as represented in FIGS. 1 and 3. The conductivity output signals of probes 38 and 42 are relayed separately to a process controller 46 by electrical connections 50 and 54 respectively. Process controller 46 is connected to an external power source, not shown, by electrical connection 62. The process controller 46, which may be any suitable microprocessor, for example, a programmable logic controller, or a proportional integral and derivative controller, is programmed to compare the output signals from the conductivity probes, and generate an output valve control signal. The output valve control signal is relayed to valve 14 by electrical connection 58. Valve 14, which can be an electromagnetically controlled valve, is adjusted in response to the output valve control signal, thereby controlling the amount of the conductivity increasing substance, e.g., free available chlorine, added to the fourth aqueous stream. In one embodiment of the present invention, the process controller 46 is a model number 53SL6000 MICRO-DCI™ proportional integral and derivative controller commercially available from Bailey-Fischer & Porter GmbH.

By conductivity increasing substances is meant a substance or substances that when added to an aqueous stream or body of water will result in a measurable and reproducible increase in the conductivity of the aqueous stream or body of water. The conductivity increasing substance, or its source thereof, may be in the form of a solid, liquid or gas. It is preferred that the conductivity increasing substance be substantially soluble in the aqueous medium to which it is added.

Classes of conductivity increasing substances, the amount of which present in an aqueous medium may be controlled by the method of the present invention include, but are not limited to: organic acids, e.g., acetic acid, lactic acid, and citric acid; salts of organic acids, e.g., sodium acetate, and sodium lactate; inorganic acids, e.g., hydrogen halides, such as, hydrochloric acid and hydrobromic acid, and hypohalous acids, such as, hypochlorous acid and hypobromous acid; salts of inorganic acids, e.g., sodium chloride, potassium chloride, sodium bromide, potassium bromide, and the salts of hypohalous acids described hereinafter; bases, e.g., sodium hydroxide, potassium hydroxide, sodium carbonate, and sodium bicarbonate; sanitizing agents, e.g., sodium hypochlorite, potassium hypochlorite, lithium hypochlorite, chlorine gas, bromo-chloro dimethylhydantoin, dichlorohydantoin, povidone-iodine, and chlorinated isocyanurates, including trichloroisocyanuric acid; reducing agents, i.e., desanitizing agents (dehalogenation, i.e., dechlorination and debromination), e.g., sodium sulfite, sodium metabisulfite, sodium bisulfite, sodium thiosulfate, sodium sulfhydrate (NaSH), and sodium hydrogen sulfide ($Na_2S$); and quaternary ammonium compounds, e.g., tetrabutylammonium chloride, and tetrabutylammonium bromide.

When mixtures of conductivity increasing substances are added to an aqueous medium, the interaction if any between the substances should be taken into consideration. For example, if acids and bases are added to the same aqueous medium, the resulting change in electrical conductivity may not be an increase equivalent to the sum of the conductivities resulting from separate additions of the acids and bases.

In one embodiment of the present invention, the source of the conductivity increasing substance is selected from the group consisting of calcium hypochlorite, sodium hypochlorite, potassium hypochlorite, lithium hypochlorite, chlorine gas, and mixtures thereof. In a preferred embodiment of the present invention, the source of the conductivity increasing substance is a source of free available halogen. By free available halogen is meant halogen that is present in the aqueous solution in an oxidized form. Free available halogen (FAH) is present in the form of hypohalous acid (HOX) and/or hypohalite anion ($XO^-$), wherein X represents a halogen group having a +1 oxidation state. The halogen, X, of the free available halogen is selected from the group consisting of chlorine, bromine and iodine. In a particularly preferred embodiment of the present invention, the source of free available halogen is selected from the group consisting of calcium hypochlorite, sodium hypochlorite, potassium hypochlorite, lithium hypochlorite, chlorine gas, and mixtures thereof, and the feeder unit is a chlorination unit.

In a preferred embodiment of the present invention, the minimum amount of free available chlorine (FAC) added to the fourth aqueous stream which is forwarded through conduit 34 of FIG. 1, is typically 10 parts FAC per million parts of the fourth aqueous stream (ppm), preferably 30 ppm, more preferably 50 ppm, and particularly more preferably 100 ppm. The maximum amount of FAC added to an aqueous stream in accordance with the method of the present invention is typically 100,000 ppm, preferably 10,000 ppm, more preferably 5000 ppm, and particularly more preferably 1000 ppm. The amount of FAC added to the fourth aqueous stream, in accordance with the method of the present invention, may range between any of these recited minimum and maximum values. While the method of the present invention can be used to control the addition of FAC in amounts less than 10 ppm, the limitations of currently available equipment make such additions inaccurate.

The feeder unit 26 may be any appropriate unit suitable for adding conductivity increasing substances to an aqueous stream in a substantially constant manner. In a preferred embodiment of the present invention, feeder unit 26 is a chlorination unit. By chlorination unit is meant a unit which is capable of adding free available chlorine to an aqueous stream. The FAC or source of FAC may be present within or introduced into the feeder unit 26, through a port not shown, in solid form, e.g., calcium hypochlorite, liquid form, e.g., a concentrated aqueous solution of sodium or calcium hypochlorite, or gaseous form, e.g., chlorine gas. In a particularly preferred embodiment of the present invention, the feeder unit 26 is a chlorination unit, as described in U.S. Pat. No. 5,384,102, the disclosure of which is incorporated herein in its entirety.

The present invention is also directed to a method of sanitizing a surface of an article. With reference to FIG. 1, the fourth aqueous stream passing through conduit 34, to which free available halogen, e.g., free available chlorine, has been added, can be delivered to a holding tank or to one or more spray nozzles not shown. The aqueous stream having FAC added thereto, i.e., a sanitizing aqueous stream, is applied to the surface to be sanitized.

The sanitizing aqueous stream may be applied by any appropriate method, examples of which include but are not limited to: spray application; wiping with soaked rags; curtain or waterfall application; and soaking by immersion. Examples of surfaces or articles which may be sanitized by the method of the present invention include, but are not limited to: harvested vegetables such as potatoes, sweet potatoes, and mushrooms; harvested fruits, such as apples; metal surfaces in meat processing plants; equipment in breweries, e.g., fermenting tubs, and the interior and exterior of pipes; and chicken carcasses in chicken processing plants.

The present invention is more particularly described in the following examples, which are intended to be illustrative only, since numerous modifications and variations therein will be apparent to those skilled in the art. Unless otherwise specified, all parts and percentages are by weight.

EXAMPLE

Figure 2:
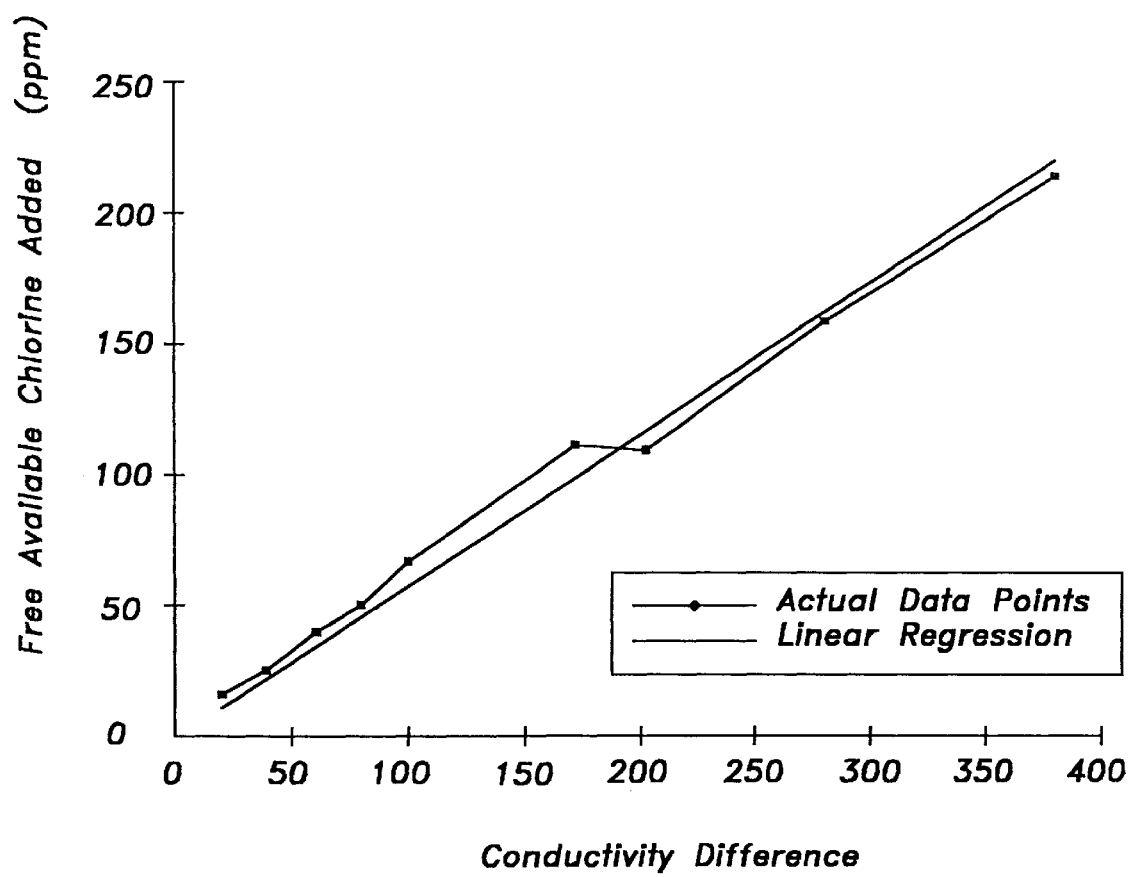
FIG. 2 is a graph showing a plot of the amount of free available chlorine present in an aqueous stream vs. electrical conductivity difference; also shown is a line resulting from a linear regression analysis of the actual data.

This example describes the controlled addition of different amounts of free available chlorine (FAC) to an aqueous stream according to an embodiment of the method of the present invention. The data obtained is shown in Table 1 and a graph of the plotted data is shown in FIG. 2 of the drawings.

A water distribution system similar to that represented in FIG. 3 of the drawings was used, and this example will be described with reference to it. The process controller 46 was not used, and valve 14 was operated manually. Valve 14 was an electrically actuated ball valve obtained from Neles-Jamesbury Inc., model number EHX20. The addition unit 26 used was a chlorinator available from PPG Industries, Inc., model number 3150. Tablets of calcium hypochlorite, obtained from PPG Industries, Inc., were placed inside of the chlorinator prior to the introduction of the first aqueous stream therein.

The pressure of the aqueous stream introduced into conduit 10 was sufficiently low that the pressure regulator 70 was not required and was not present. The third aqueous stream exiting conduit 82, and the second aqueous stream exiting conduit 22 were combined in collection tank 102. The fourth aqueous stream was drawn from collection tank 102 through conduit 98 and introduced into conduit 34 by pump 94.

The conductivity probes 38 and 42 were inserted directly into conduits 10 and 34 respectively. The probes were obtained from Bailey-Fischer & Porter GmbH, model number TB461, and were each connected to a separate indicating transmitter, also obtained from Bailey-Fischer & Porter GmbH, model number TB440. Conductivity values were read directly from the indicating transmitters.

The aqueous stream introduced into conduit 10 was drawn from a 37,000 liter pool of water. The fourth aqueous stream exiting through conduit 34, to which free available chlorine had been added, was run back into the same pool of water. The flow of the aqueous stream introduced into the chlorinator 26 was increased in stages by manually adjusting valve 14 at periodic intervals. Following an adjustment to valve 14, the conductivity output signals from probes 38 and 42 were recorded after waiting a minimum of five minutes to ensure equilibration about the chlorinator. At the same time, samples of the aqueous streams passing through conduits 10 and 34 were taken, and the amount of free available chlorine in each sample was measured by iodometric titration in accordance with test method 4500-Cl B of the *Standard Methods for the Examination of Water and Wastewater*, 19th edition, 1995, American Public Health Association, Library of Congress Catalog Card Number: 95-79480. From these recorded data, the amount of free available chlorine added to the aqueous stream and the resulting increase in conductivity were calculated and tabulated in Table 1.

A plot of the free available chlorine added to the aqueous stream vs. conductivity difference was obtained from the data tabulated in Table 1, as represented by the graph shown in FIG. 2 of the drawings. A plot resulting from a linear regression analysis of the data of Table 1 is also shown in the graph of FIG. 2. Setting the intercept of the y axis equal to zero, the linear regression analysis resulted in a line having a slope of 0.5645 and a coefficient of determination equal to 0.9869. A coefficient of determination of 1.0000 indicates that the data upon which the linear regression analysis was performed would result in a perfectly straight line. As such the calculated coefficient of determination of 0.9869 indicates that the relationship between the free available chlorine added to the aqueous stream and the resulting conductivity difference is essentially a linear one.

TABLE 1

| Conductivity Difference | Free Available Chlorine Added to the Aqueous Stream (ppm)[a] |
| --- | --- |
| 20 | 16 |
| 40 | 25 |
| 60 | 40 |
| 80 | 57 |
| 100 | 67 |
| 170 | 109 |
| 200 | 107 |
| 280 | 155 |
| 380 | 209 |

[a]ppm = parts free available chlorine per million parts of water.

The data of Table 1 and their graphical representation in FIG. 2 of the drawings demonstrates the operability of the method of the present invention with regard to its use in controlling the amount of conductivity increasing substances, e.g., free available chlorine, added to an aqueous stream. The relationship between the amount of free available chlorine added to the aqueous stream and the resulting conductivity difference is shown to be substantially linear.

The present invention has been described with reference to specific details of particular embodiments thereof. It is not intended that such details be regarded as limitations upon the scope of the invention except insofar as and to the extent that they are included in the accompanying claims.

We claim:

1. A method of controlling the amount of conductivity increasing substance present in an aqueous stream, comprising the steps of:
   (a) providing a feeder unit having therein a source of at least one conductivity increasing substance;
   (b) providing an aqueous stream;
   (c) splitting said aqueous stream into a first aqueous stream and a second aqueous stream;
   (d) introducing controllably said first aqueous stream into said feeder unit and into contact with said conductivity increasing substance;
   (e) removing a third aqueous stream from said feeder unit, said third aqueous stream containing said conductivity increasing substance;
   (f) combining said third aqueous stream with said second aqueous stream to form a fourth aqueous stream;
   (g) determining the electrical conductivities of the aqueous stream of step (b) and of said fourth aqueous stream;
   (h) comparing the conductivities determined in step (g); and
   (i) adjusting in response to the comparison of step (h) the introduction of said first aqueous stream into said feeder unit, thereby controlling the amount of said conductivity increasing substance present in said fourth aqueous stream.

2. The method of claim 1 wherein said source of conductivity increasing substance is selected from the group consisting of calcium hypochlorite, sodium hypochlorite, potassium hypochlorite, lithium hypochlorite, chlorine gas, and mixtures thereof, and said feeder unit is a chlorination unit.

3. The method of claim 2 wherein said source of conductivity increasing substance is calcium hypochlorite.

4. The method of claim 3 wherein from 10 to 100,000 parts of free available chlorine per million parts of said aqueous stream are added to said aqueous stream.

5. The method of claim 1 wherein a remotely controlled valve is used to introduce controllably said first aqueous stream into said feeder unit.

6. The method of claim 5 wherein steps (g), (h) and (i) are governed by a process controller.

7. A method of controlling the amount of free available halogen present in an aqueous stream, comprising the steps of:
   (a) providing a halogenation unit having therein a source of free available halogen;
   (b) providing an aqueous stream;
   (c) splitting said aqueous stream into a first aqueous stream and a second aqueous stream;
   (d) introducing controllably said first aqueous stream into said halogenation unit and into contact with said source of free available halogen;
   (e) removing a third aqueous stream from said halogenation unit, said third aqueous stream containing free available halogen;

(f) combining said third aqueous stream with said second aqueous stream to form a fourth aqueous stream;

(g) determining the electrical conductivities of the aqueous stream of step (b) and of said fourth aqueous stream;

(h) comparing the conductivities determined in step (g); and (i) adjusting in response to the comparison of step (h) the introduction of said first aqueous stream into said halogenation unit, thereby controlling the amount of free available halogen present in said fourth aqueous stream.

8. The method of claim 7 wherein the halogen of the free available halogen is selected from the group consisting of chlorine, bromine, and iodine.

9. The method of claim 8 wherein said source of free available halogen is selected from the group consisting of calcium hypochlorite, sodium hypochlorite, potassium hypochlorite, lithium hypochlorite, chlorine gas, and mixtures thereof, and said halogenation unit is a chlorination unit.

10. The method of claim 9 wherein said source of free available halogen is calcium hypochlorite.

11. The method of claim 10 wherein from 10 to 100,000 parts of free available chlorine per million parts of said aqueous stream are added to said aqueous stream.

12. The method of claim 11 wherein a remotely controlled valve is used to introduce controllably said first aqueous stream into said chlorination unit.

13. The method of claim 12 wherein steps (g), (h) and (i) are governed by a process controller.

14. A method of sanitizing a surface comprising:

(a) controlling the amount of free available halogen present in an aqueous stream by the steps of:

(i) providing a halogenation unit having therein a source of free available halogen;

(ii) providing an aqueous stream;

(iii) splitting said aqueous stream into a first aqueous stream and a second aqueous stream;

(iv) introducing controllably said first aqueous stream into said halogenation unit and into contact with said source of free available halogen;

(v) removing a third aqueous stream from said halogenation unit, said third aqueous stream containing free available halogen;

(vi) combining said third aqueous stream with said second aqueous stream to form a fourth aqueous stream;

(vii) determining the electrical conductivities of the aqueous stream of step (a)(ii) and of said fourth aqueous stream;

(viii) comparing the conductivities determined in step (a)(vii); and (ix) adjusting in response to the comparison of step (a)(viii) the introduction of said first aqueous stream into said halogenation unit, thereby controlling the amount of free available halogen present in said fourth aqueous stream; and (b) applying said fourth aqueous stream to a surface to be sanitized.

15. The method of claim 14 wherein the halogen of the free available halogen is selected from the group consisting of chlorine, bromine, and iodine.

16. The method of claim 15 wherein said source of free available halogen is calcium hypochlorite, and said halogenation unit is a chlorination unit.

17. The method of claim 16 wherein from 10 to 100,000 parts of free available chlorine per million parts of said aqueous stream are added to said aqueous stream.

* * * * *